(12) United States Patent
Weil et al.

(10) Patent No.: US 6,216,024 B1
(45) Date of Patent: *Apr. 10, 2001

(54) METHOD AND DEVICE FOR ASSESSING PERFUSION FAILURE IN A PATIENT

(75) Inventors: Max Harry Weil, Northbrook, IL (US); Wanchun Tang, Palm Desert; Jose Bisera, Camarillo, both of CA (US)

(73) Assignee: Institute of Critical Care Medicine, Palm Springs, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/160,224

(22) Filed: Sep. 24, 1998

Related U.S. Application Data

(63) Continuation-in-part of application No. 09/099,293, filed on Jun. 18, 1998, now Pat. No. 6,055,447, which is a continuation-in-part of application No. 08/939,591, filed on Sep. 29, 1997, now abandoned, which is a continuation-in-part of application No. 08/710,208, filed on Sep. 13, 1996, now abandoned, which is a continuation-in-part of application No. 08/498,932, filed on Jul. 6, 1995, now Pat. No. 5,579,763.

(51) Int. Cl.$^7$ ........................................................ A61B 5/00
(52) U.S. Cl. ............................................................. 600/353
(58) Field of Search ................................... 300/345–350, 300/309, 300–301, 529, 587, 353–4

(56) References Cited

U.S. PATENT DOCUMENTS 3,905,889   9/1975   Macur et al. .
4,016,863   4/1977   Brantigan .

(List continued on next page.)

FOREIGN PATENT DOCUMENTS

WO 94/23645   10/1994   (WO) .

OTHER PUBLICATIONS

Jin et al. (1997), "End–Tidal $PCO_2$ Serves as an Indicator of Cardiac Output During Experimental Septic Shock," *Crit. Care Med* 25(1):A122 (Abstract).

Nakagawa et al. (1997), "Sublingual Capnometry for Quantitation of the Severity of Hemorrhagic Shock," *Shock* 7:14 (Abstract).

Nakagawa et al. (1997), "$ETCO_2$ as Non–Invasive Indicator of Cardiac Output During Hemorrhagic Shock," *Crit. Care Med.* 25(1):A132 (Abstract).

Nakagawa et al. (1997), "Sublingual Capnography as an Indicator of Perfusion Failure In Human Patients," *Chest* 112:4S (Abstract).

(List continued on next page.)

*Primary Examiner*—Robert L. Nasser
(74) *Attorney, Agent, or Firm*—Dianne E. Reed; Reed & Associates

(57) ABSTRACT

Methods and devices are provided for assessing impairment of blood circulation in a patient, such as that in perfusion failure, by measurement of $pCO_2$ (partial pressure of carbon dioxide) in the upper digestive and/or respiratory tract of the patient. The method comprises introducing a carbon dioxide sensor into the upper digestive and/or respiratory tract of a patient, without passing the sensor down through or beyond the patient's epiglottis. Specifically, a carbon dioxide sensor is placed adjacent a mucosal surface within the upper digestive and/or respiratory tract, preferably within the patient's mouth or inside the patient's nose. By avoiding passage through the mouth into the throat and esophagus, discomfort is substantially avoided and the potential for injury minimized. Previously, the belief in the art was that increased partial pressure of carbon dioxide was a localized phenomenon during perfusion failure; however, applicants have now discovered that increases in tissue $CO_2$ occur throughout the body during perfusion failure, and the method and device of the invention are premised on this discovery.

14 Claims, 7 Drawing Sheets

U.S. PATENT DOCUMENTS

| | | |
|---|---|---|
| 4,381,011 | 4/1983 | Somers, 3rd . |
| 4,503,859 | 3/1985 | Petty et al. . |
| 4,535,786 | 8/1985 | Kater . |
| 4,577,109 | 3/1986 | Hirschfeld . |
| 4,632,119 | 12/1986 | Reichstein . |
| 4,643,192 | 2/1987 | Fiddian-Green . |
| 4,729,824 | 3/1988 | Giner . |
| 4,785,814 | 11/1988 | Kane . |
| 4,789,453 | 12/1988 | Eberhard et al. . |
| 4,816,131 | 3/1989 | Bomsztyk . |
| 4,833,091 | 5/1989 | Leader et al. . |
| 4,834,101 | 5/1989 | Collison et al. . |
| 4,842,783 | 6/1989 | Blaylock . |
| 4,890,619 | 1/1990 | Hatschek . |
| 4,892,383 | 1/1990 | Klainer et al. . |
| 4,919,891 | 4/1990 | Yafuso et al. . |
| 4,981,470 | 1/1991 | Bombeck, IV . |
| 5,006,314 | 4/1991 | Gourley et al. . |
| 5,098,659 | 3/1992 | Yim et al. . |
| 5,105,812 | 4/1992 | Corman . |
| 5,117,827 | 6/1992 | Stuebe et al. . |
| 5,158,083 | 10/1992 | Sacristan et al. . |
| 5,174,290 | 12/1992 | Fiddian-Green . |
| 5,251,619 * | 10/1993 | Lee ........................................ 600/350 |
| 5,280,548 | 1/1994 | Atwater et al. . |
| 5,329,922 | 7/1994 | Atlee, III . |
| 5,330,718 | 7/1994 | Hui et al. . |
| 5,341,803 | 8/1994 | Goldberg et al. . |
| 5,368,027 | 11/1994 | Lübbers et al. . |
| 5,408,999 | 4/1995 | Singh et al. . |
| 5,411,022 | 5/1995 | McCue et al. . |
| 5,423,320 | 6/1995 | Salzman et al. . |
| 5,453,248 | 9/1995 | Olstein . |
| 5,456,251 | 10/1995 | Fiddian-Green . |
| 5,479,923 | 1/1996 | Rantala . |
| 5,579,763 | 12/1996 | Weil et al. . |
| 5,596,988 | 1/1997 | Markle et al. . |
| 5,631,340 | 5/1997 | Olstein . |
| 5,714,121 | 2/1998 | Alderete et al. . |
| 5,743,259 * | 4/1998 | Kruse et al. ......................... 600/309 |
| 5,788,631 | 8/1998 | Fiddian-Green . |

OTHER PUBLICATIONS

Nakagawa et al. (1998), "Comparison of Sublingual Capnometry with Gastric Capnometry and Lactate as Indicators of the Severity of Hemorrhagic Shock," *Crit. Care Med.* 26(1):A44 (Abstract).

Ogino et al. (1994), "Relfectance Pulse Oximeter Measuring Central SaO2 From Mouth," Proceedings of the Annual International Conference of the IEEE Engineering in Medicine and Biology Society, Baltimore, 2(16):914–915.

Peterson et al. (1984), "Fiber Optic Sensors for Biomedical Applications," *Science* 224(4645):123–127.

Sato et al. (1997), "Esophageal and Gastric $PCO_2$ Both Serve as Quantitative Indicators of Organ Blood Flow During Hemorrhagic Shock," *Crit. Care Med.* 25(1):A37 (Abstract).

Sato et al. (1997), "Esophageal $PCO_2$ as a Monitor of Perfusion Failure During Hemorrhagic Shock," *J. Appl. Physiol.* 82(2):558–562.

Seitz (1984), "Chemical Sensors Based on Fiber Optics," *Anal. Chem.* 56(1):16A–34A.

Tang et al. (1998), "Myocardial Preservation During Cardiopulmonary Resuscitation," *Curr. Opin. Crit. Care* 4:155–160.

Weil (1998), "The Assault on the Swan–Ganz Catheter," *Chest* 113:1379–1386(1998) (Invited Publication).

Xie et al. (1997), "Sublingual Capnometry for Quantitation of the Severity of Septic Shock," *Shock* 7:13–14 (Abstract).

* cited by examiner

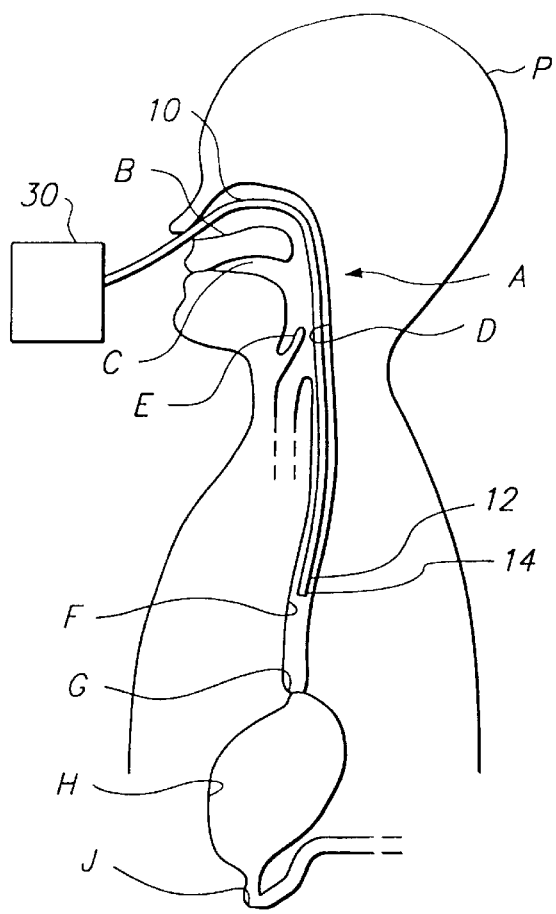
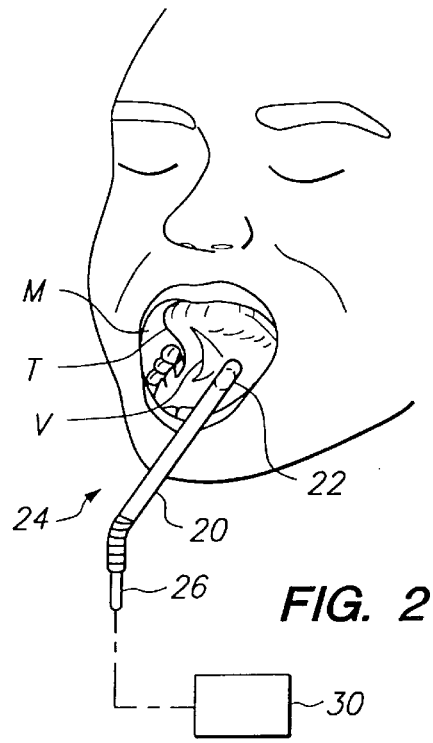
FIG. 1
FIG. 2
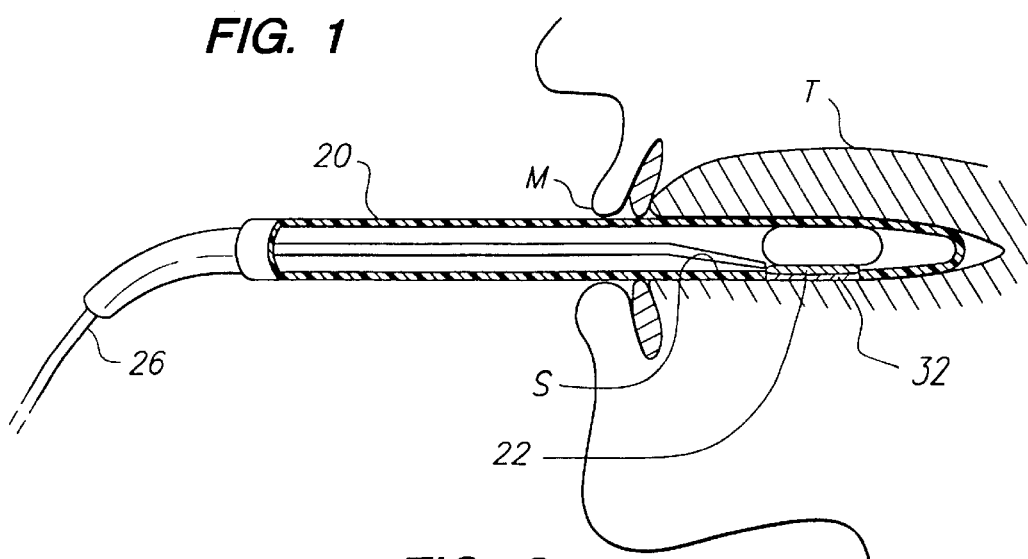
FIG. 3

|  |  | PATIENT CONDITION | | |
|---|---|---|---|---|
|  |  | RED | YELLOW | GREEN |
| PCO2 RANGE | TREND | POOR | GUARDED | STABLE |
| $pCO_2 > Z$ | Positive | X | | |
|  | None | X | | |
|  | Negative | | X | |
| $Y < pCO_2 < Z$ | Positive | X | | |
|  | None | | X | |
|  | Negative | | X | |
| $pCO_2 < Y$ | Positive | | X | |
|  | None | | | X |
|  | Negative | | X | |

*FIG. 10*

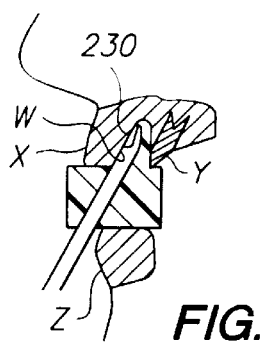
FIG. 13
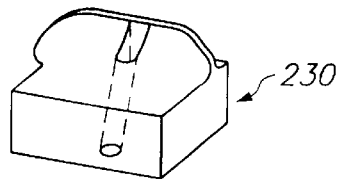
FIG. 14
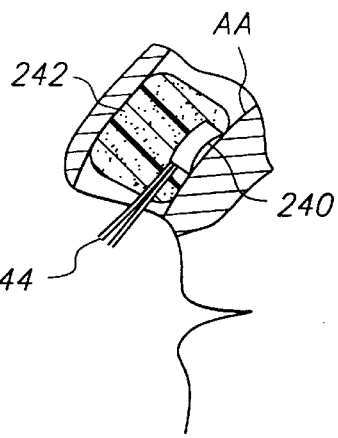
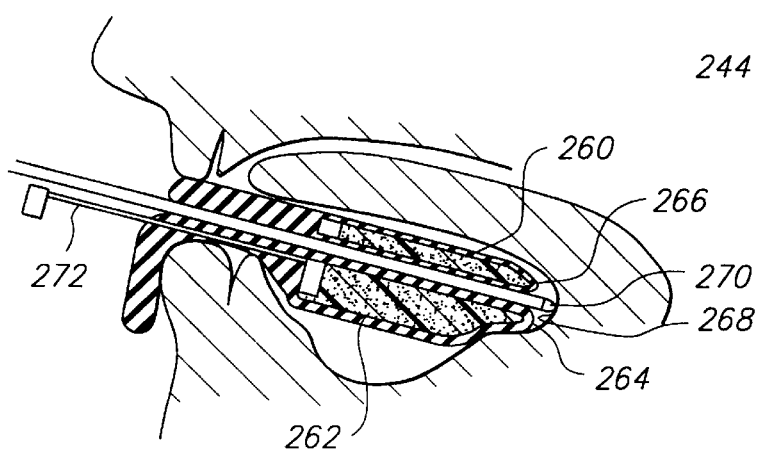
FIG. 15
FIG. 16
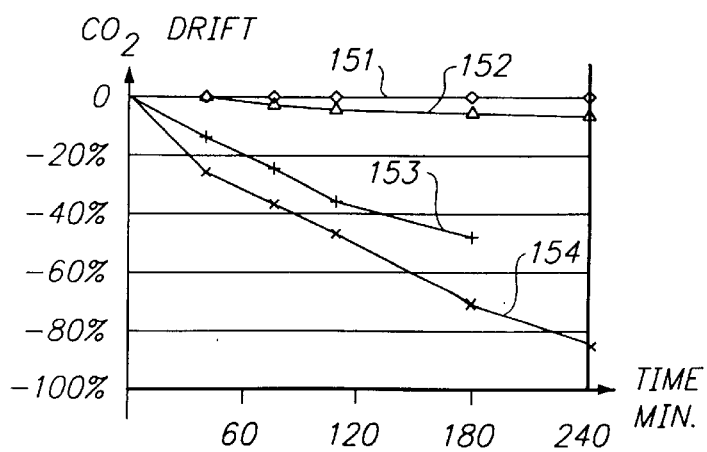
FIG. 17

METHOD AND DEVICE FOR ASSESSING PERFUSION FAILURE IN A PATIENT

CROSS-REFERENCE TO RELATED APPLICATIONS

This application is a continuation-in-part of U.S. Ser. No. 09/099,293, filed Jun. 18, 1998, now U.S. Pat. No. 6,055,447 and of U.S. Ser. No. 08/939,591, filed Sep. 29, 1997, now abandoned which was a continuation-in-part of U.S. Ser. No. 08/710,208, filed Sep. 13, 1996, abandoned, which was a continuation-in-part of U.S. Ser. No. 08/498,932, filed Jul. 6, 1995, which issued Dec. 3, 1996 as U.S. Pat. No. 5,579,763, each of which patent applications and patents are incorporated herein by reference.

TECHNICAL FIELD

The present invention relates generally to methods and devices for assessing perfusion failure in a patient. More particularly, the invention relates to assessment of perfusion failure in a patient by measuring the localized partial pressure of carbon dioxide within the upper respiratory/digestive tract of a patient.

BACKGROUND

Very low blood flow, or low "systemic perfusion," is typically due to low aortic pressure and can be caused by a number of factors, including hemorrhage, sepsis and cardiac arrest. When there is a reduced flow of blood from the heart, the body directs a higher portion of blood to critical organs, such as the brain, which will not survive long without a continuous supply of blood, while restricting the flow to less critical organs, such as the stomach and intestines, whose survival is not as threatened by a temporary large reduction in blood flow. Physicians commonly take advantage of this phenomenon by taking measurements in the stomach and intestine to assess perfusion failure.

Assessment of $CO_2$ concentration in the less critical organs, i.e., those organs to which blood flow is reduced during perfusion failure, is useful in perfusion assessment. Carbon dioxide production, which is associated with metabolism, continues even during low blood flow. Because $CO_2$ is not rapidly carried away during low blood flow, the concentration of $CO_2$ increases, which in turn results in a decrease in pH and an increase in partial pressure of $CO_2$ ($pCO_2$) in the less critical organs. Therefore, perfusion failure is commonly assessed by measuring pH or $pCO_2$ at these sites, especially in the stomach and intestines. For examples of catheters used to assess pH or $pCO_2$ in the stomach or intestines, see, e.g., U.S. Pat. Nos. 3,905,889; 4,016,863; 4,632,119; 4,643,192; 4,981,470; 5,105,812; 5,117,827; 5,174,290; 5,341,803; 5,411,022; 5,423,320; 5,456,251; and 5,788,631.

The measurement of $pCO_2$ to determine the extent of perfusion failure has commonly been done by threading a catheter through the nasal passage, past the epiglottis, through the esophagus, past the esophageal sphincter, and into the stomach, and sometimes through the stomach and into the intestines. Alternatively, measurement has been conducted in the colon, with a catheter being threaded through the anus. These procedures are obviously quite invasive and can cause harm and discomfort to a patient. Moreover, insertion of the catheter in this manner is also complex and time-consuming.

In U.S. Pat. No. 5,579,763, applicants described the introduction of a catheter with a carbon dioxide sensor through the nasal or oral passage, past the epiglottis, and into the esophagus so that the catheter and sensor lay within the esophagus. This method can be used to accurately assess perfusion failure by measuring $pCO_2$ in the patient's esophagus of a patient, rather than in the stomach and/or intestine. Tests showed that measurements of $pCO_2$ in the esophagus are closely correlated with aortic pressure, and, furthermore, that measurements made in the esophagus are even more closely correlated to aortic pressure than measurements of $CO_2$ in the stomach. This procedure was advantageous in that the procedure's invasiveness was reduced and $CO_2$ generated by digestive fluids in the stomach did not affect measurements since the esophageal sphincter blocks such gas. However, the insertion of the catheter still constituted considerable invasion and thus risk of harm to the patient. Furthermore, extension of the catheter extended past the epiglottis exposed the patient to the risk of regurgitation of stomach contents including stomach acids.

There is a need for an even less invasive method to measure perfusion failure and to monitor the effectiveness of methods taken to increase perfusion, e.g., blood infusion or the like.

SUMMARY OF THE INVENTION

Methods and devices are provided for assessing impairment of blood circulation in a patient, such as that in perfusion failure, by measurement of $pCO_2$ (partial pressure of carbon dioxide) in the upper digestive and/or respiratory tract of the patient. The method comprises introducing a carbon dioxide sensor into the upper digestive and/or respiratory tract of a patient, without passing the sensor down through or beyond the patient's epiglottis. Specifically, a carbon dioxide sensor is placed adjacent a mucosal surface within the upper digestive and/or respiratory tract, preferably within the patient's mouth or inside the patient's nose. By avoiding passage through the mouth into the throat and esophagus, discomfort is substantially avoided and the potential for injury minimized. Previously, the belief in the art was that increased partial pressure of carbon dioxide was a localized phenomenon during perfusion failure; however, applicants have now discovered that increases in tissue $CO_2$ occur throughout the body during perfusion failure, and the method and device of the invention are premised on this discovery.

Applicants prefer to introduce the carbon dioxide sensor sublingually, and preferably to one side of the frenulum. The invasiveness of such a technique is minimal, being substantially no more than in the use of an oral thermometer. The sensor preferably lies at the inner end of a holder that lies stably in the patient's mouth. The holder maintains the sensor in position, and also isolates the area immediately surrounding the mucosal surface contacted by the sensor from surrounding air flow that could carry away some $CO_2$ and result in an incorrect measurement. Preferably, the sensor is an optical $CO_2$ sensor. The output of the sensor can be detected by a device which electronically converts the sensor output to provide a $CO_2$ concentration value. The device can further sense the rate of change of $CO_2$ concentration with time to indicate the patient's condition.

Accordingly, in one aspect the invention features a device for assessing perfusion failure in a patient, where the device is composed of a carbon dioxide sensor means for detecting a partial pressure of carbon dioxide ($pCO_2$), the sensor means being adapted for lying adjacent a mucosal surface of the upper respiratory/digestive tract of a patient and measuring carbon dioxide at the mucosal surface; and an indicating means connected to the sensor means, wherein the indicating means indicates a degree of perfusion failure of the patient associated with the detected partial pressure of carbon dioxide. Preferably the device also includes an isolating means for inhibiting air flow around the mucosal surface in a region surrounding the sensor means.

In a preferred embodiment, the isolating means is a holder designed to fit within the mouth of the patient and hold the sensor in place adjacent the mucosal surface. The holder may be designed to contact the bottom of the tongue and the floor of the mouth of the patient, or to fit between the inside of a lip and gum of the patient. In another embodiment, the isolating means is a holder designed to fit within a nares of the patient and hold the sensor in place adjacent the mucosal surface.

In another preferred embodiment, the device includes a moisturizing means for supplying moisture to the mucosal surface adjacent the sensor.

In a second aspect the invention features a device for use with a $pCO_2$ sensor assembly for assessing perfusion failure of a patient. The device is composed of a sensor holder with a sublingual holder inner portion shaped to fit in the mouth of a patient under the patient's tongue, said holder forming at least one holder passage extending from said holder outer portion to said sublingual holder portion.

In another aspect the invention features a method for assessing perfusion failure of a patient, the method involving the steps of placing a carbon dioxide sensor adjacent a mucosal surface of an upper digestive/respiratory tract of a patient, and measuring a partial pressure of carbon dioxide at the mucosal surface. A partial pressure of carbon dioxide at the mucosal surface of the upper digestive/respiratory tract that is substantially greater than a normal partial pressure of carbon dioxide is indicative of perfusion failure in the patient. In preferred embodiments the mucosal surface is within the mouth or nose of the patient.

One advantage of the invention is that perfusion can be assessed in a patient in a minimally invasive manner, and with minimal discomfort or risk of harm to the patient.

Another advantage of the invention is that perfusion can be readily assessed in a patient suffering from perfusion failure associated with any of a variety of causes, including, but not limited to physical trauma, infection, hypothermia, cardiogenic shock (e.g., acute myocardial infarction, aneurysm, or arrhythmia), obstructive shock (e.g., pulmonary embolism), hypovolemic shock (e.g., due to hemorrhage or fluid depletion), and distributive shock (e.g., due to sepsis, exposure to toxins, or anaphylaxis). The sensitivity of the methods and devices of the invention further allow for assessment of perfusion across a wide range of perfusion failure severity, thereby providing a means to accurately monitor the patient's condition.

Still another advantage of the invention is that the devices and methods can be readily adapted for use in alert, semiconscious, or unconscious patients, and can be further adapted for accurate assessment of perfusion in a patient for a period lasting for only minutes to hours or days.

The novel features of the invention are set forth with particularity in the appended claims. The invention will be best understood from the following description when read in conjunction with the accompanying drawings.

BRIEF DESCRIPTION OF THE DRAWINGS

FIG. 1 is a partial sectional view of the digestive system of a patient (including the nasal passage), and showing a previous sensor of applicant which is fully installed during a test.

FIG. 2 is an isometric view showing a sensor of the present invention as it is introduced into the mouth of a patient, for sublingual placement.

FIG. 3 is a sectional view showing the sensor of FIG. 2 fully installed in a patient's mouth.

FIG. 10 is a chart that shows the logic of the circuit of FIG. 9.

FIG. 13 is a sectional view of a sensor assembly and holder of another embodiment of the invention, shown holding a sensor between a lip and teeth of a patient.

FIG. 14 is a front isometric view of the holder of FIG. 13.

FIG. 15 is a sectional view of a sensor assembly and holder of another embodiment of the invention, shown holding a sensor in the nose of a patient.

FIG. 16 is a sectional view of a sensor assembly and holder of another embodiment of the invention, where the holder can add moisture to the area of the sensor.

FIG. 17 is a graph showing $CO_2$ sensor drift with time in different environments.

DETAILED DESCRIPTION OF THE INVENTION

Figure 4:
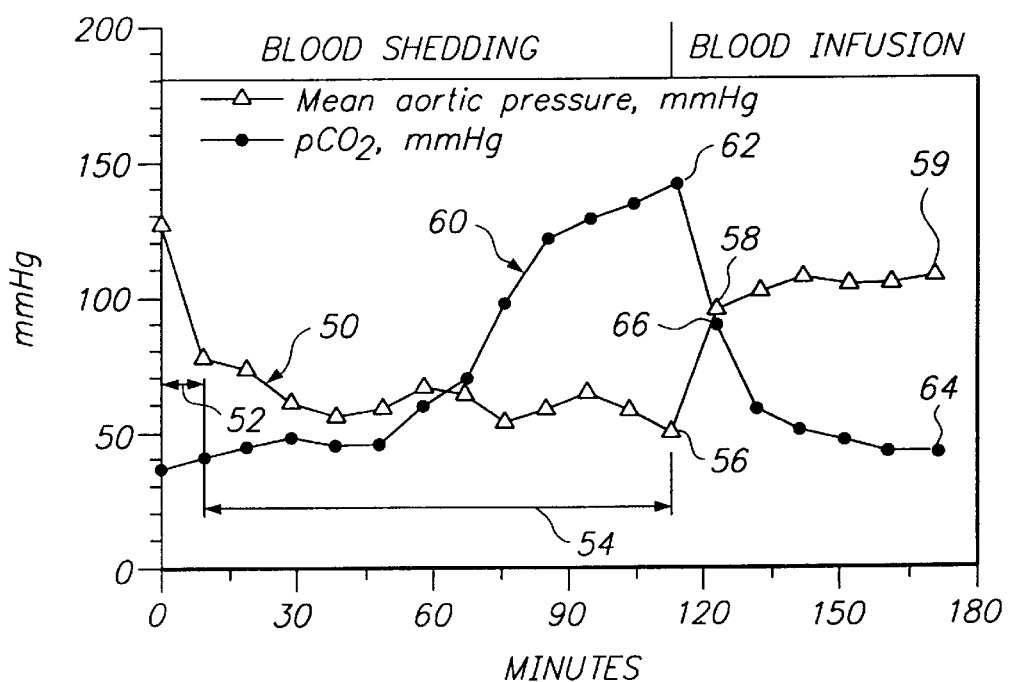
FIG. 4 is a graph that includes a graph line showing variation in aortic pressure with time, and that also includes a graph line showing variation in sublingual $pCO_2$ measurement with time, during an experiment on a rat.

Definitions and nomenclature:

Before the present compounds, compositions and methods are disclosed and described, it is to be understood that this invention is not limited to sensor designs, measurement techniques, or the like, as such may vary. It is also to be understood that the terminology used herein is for the purpose of describing particular embodiments only and is not intended to be limiting.

It must be noted that, as used in the specification and the appended claims, the singular forms "a," "an" and "the" include plural referents unless the context clearly dictates otherwise.

The term "perfusion failure" as used herein is meant a reduction in blood flow associated with maldistribution of blood through the circulatory system and a reduction in blood flow to a less critical tissue(s) and/or organ(s) relative to blood flow in vital (critical) tissues and organs (e.g., the brain and heart). In general, "perfusion failure" is meant to encompass reduction in blood flow associated with a increase in $pCO_2$ of significantly or substantially above a $pCO_2$ associated with normal perfusion.

The term "measurement" as used herein refers to a single measurement or a series of measurements made over time, and which may be taken continuously or intermittently (e.g., at selected time intervals).

The term "sample fluid" as used herein refers to a liquid or gaseous material (e.g., vapor, mist, or gas) that may be analyzed using the sensors disclosed herein. Generally, "sample fluids" analyzed in the course of assessing perfusion failure will be a mixture of gas and fluid trapped within the area defined by the sensor holder walls and a mucosal surface with which the sensor holder is in contact.

The term "upper respiratory/digestive tract" as used herein means the region of the upper respiratory tract and digestive tract at the surface or and above the epiglottis. In general, the "upper respiratory/digestive tract" encompasses the nasal passages (including the nares and nasal cavities), the oral passage (including the mouth and spaces within the mouth such as the floor (e.g., sublingual area) and roof of the mouth (e.g., hard palate), the soft palate, the regions between the lips and gums, and the cheeks and gums), the nasopharynx, and the upper portion of the throat that extends to the top surface of and in the region of the epiglottis.

The term "oral-nasal cavity" as used herein means the region of the upper respiratory/digestive tract encompassing the nasal passages (including the nares and nasal cavities), the oral passage (including the mouth and spaces within the mouth such as the floor (e.g., sublingual area) and roof of the mouth (e.g., hard palate), the soft palate, the regions between the lips and gums, and the cheeks and gums), and the nasopharynx.

The term "sublingual" as used herein refers to a region below or beneath the tongue.

The term "mucosal surface" as used herein refers to a surface of a mucous membrane containing or associated with mucus secreting glands, and which lines body passages, tubular structures, and organs. In general, "mucosal surface" is meant to refer to the surface of the membranes lining the digestive and respiratory tracts.

The term "adjacent" as used herein (e.g., "adjacent the mucosal surface") means near or against, e.g., at a distance from the mucosal surface that allows acceptably accurate measurement of carbon dioxide by a carbon dioxide sensor.

The term "patient" as used herein means a mammalian subject, preferably a human subject, that has, is suspected of having, or is or may be susceptible to a condition associated with low blood flow, and thus perfusion failure.

The present invention is based on applicants' discovery that increases in tissue $CO_2$ occur throughout the body during perfusion failure, rather than as only a localized phenomenon as previously believed in the art. The methods and devices of the invention are thus designed to measure the partial pressure of $CO_2$ at a convenient site within the upper respiratory/digestive tract, and are thus performed in a minimally invasive manner. In general, the $pCO_2$ measurements are made by isolating an area of a mucosal surface at a selected site within the upper respiratory/digestive tract and using a sensor to detect $pCO_2$ at the selected site.

FIG. 1 illustrates the upper digestive/respiratory system or tract A of a person, and particularly including the nasal passage B, the oral passage C, and the upper portion D of the throat that extends to the top of the epiglottis E. The lower digestive (or gastrointestinal) tract includes the esophagus F, the esophageal sphincter G, the stomach H, and the intestines J. As discussed above, applicant earlier found that an accurate assessment of perfusion failure can be obtained by measuring the $pCO_2$ in the esophagus of a patient. These measurements involved the insertion of a catheter 10 (FIG. 1) with a $CO_2$ sensor 12 at the end, through the nasal or oral passage B, C, past the epiglottis E, and into the esophagus F. The end 14 of the catheter with the sensor 12 thereat, both lay within the esophagus. This procedure was advantageous in that the procedure's invasiveness was reduced and $CO_2$ generated by digestive fluids in the stomach did not affect measurements since the esophageal sphincter blocks such gas. However, the insertion of the catheter past the epiglottis E and into the esophagus, still constituted considerable invasion. In addition to harm that might be caused by threading the catheter into place, the fact that the catheter extended past the epiglottis E meant that the patient would also be exposed to the risk of regurgitation of stomach contents including stomach acids.

In accordance with the present invention, applicant finds that a highly useful measurement of perfusion failure can be obtained by measuring $CO_2$ in the upper digestive/respiratory tract A, with the sensor lying above, at the surface of, or at the epiglottis E so it does not have to pass by it. Preferably, the sensor is placed at a site within the oral-nasal cavity, e.g., within a nasal cavity, the mouth (e.g., under the tongue at a site in contact with the tongue or the floor of the mouth, between a region of the lip and gum or the cheek and gum, the roof of the mouth, or the soft palate), or the nasopharynx. Most preferably, the sensor is placed at a site that will avoid the patient's gag reflex or otherwise minimize discomfort.

The $CO_2$ sensor lies adjacent a mucosal surface in the upper digestive/respiratory tract A, in order that it effectively measures $CO_2$ in the tissue. Since carbon dioxide can readily pass through mucosal surfaces, $CO_2$ generated by metabolic activity occurring in tissue below the mucosal surface that is not carried away by blood flow readily migrates through the mucosal surface. Placement of a $CO_2$ sensor adjacent a mucosal surface of the upper digestive/respiratory tract A according to the present invention provides a very good quantification of perfusion failure at all times, including the most critical minutes after the onset of perfusion failure when treatment is likely to be most effective.

FIG. 2 shows one embodiment of a device or apparatus of the present invention, wherein a tube 20 containing a $CO_2$ sensor 22 at its front end, is inserted into the oral passage and placed under the tongue T of the patient, preferably to one side of the frenulum V. After insertion, it would be desirable if the mouth M of the patient is kept closed around the tube, so air does not circulate around the $CO_2$ sensor, which carries away some carbon dioxide. However, as with other instruments commonly inserted through the mouth, and as with a patient in a critical condition, the patient is usually unable to keep his mouth closed. Also, when the patient breathes through his nose, there is some air flow around the mouth. In such cases the device can be adapted with a holder as described below.

As illustrated in FIG. 2, the tube 20 and sensor 22 are part of an instrument 24 that includes a flexible cable 26 that extends to a test instrument 30 that typically indicates the partial pressure of $CO_2$ in millimeters of mercury (mmHg), which provides an indicia of a degree of perfusion failure. While the tube 20 is substantially rigid, the cable 26 is flexible. The cable 26 can be made highly flexible for ease of use, instead of having only the moderate flexibility of a catheter. Usually catheters require enough flexibility to pass through curved body passages, but yet must be resistant to column-type collapse in order to withstand the force applied to the catheter's proximal end necessary to accomplish insertion of the distal end and movement of the distal end along the body passage. Since the cable 26 in the device of FIG. 2 does not have to be pushed, it can have more flexibility for ease of use. The largely rigid tube 20 preferably has a length of no more than about one foot (one-third meter), since a longer length would be cumbersome. Catheters for insertion through the esophagus into the stomach, generally have a length of much more than two feet. FIG. 3 shows an example of a sensor 22, which lies against a membrane 32 which is in contact with the sublingual mucosal surface.

The correlation of perfusion failure with a increase in sublingual $pCO_2$, as well as the correlation of perfusion recovery and a decrease in sublingual $pCO_2$ was tested in an animal model that simulates a sudden loss or shedding of blood, such as might be caused by a gunshot wound or other severe wound. Perfusion recovery was simulated by subsequently reperfusing the animal with a blood infusion. The results are shown in FIG. 4. Graph line 50 (open triangles) is a measure of mean aortic pressure in mmHg throughout the test. Graph line 60 (closed circles) is a measure of sublingual $pCO_2$ obtained by a sensor.

At the beginning of the test (minutes=0), considerable blood was drawn from an animal that was previously in good health, the blood being drawn within a period of a few minutes. Graph portion 52 of graph line 50 shows that aortic pressure rapidly dropped about 30% during the first few minutes of test. In a subsequent period 54 of about two hours, the aortic pressure remained about 40% below normal. The graph 60, which shows that sublingual $pCO_2$ increased about 35% during the first 30 minutes, while aortic pressure 50 decreased by about 40%. From about 50 minutes to about 120 minutes, $pCO_2$ increased rapidly until the $pCO_2$ had increased by 300% above its initial value, as indicated by graph point 62. These data show that an increase in sublingual $pCO_2$ is inversely correlated with aortic pressure during perfusion failure.

The relationship of $pCO_2$ and aortic pressure during perfusion recovery was tested by infusing the animal with a blood infusion at 120 minutes. The animal's aortic pressure rapidly increased, as shown by graph points 56 and 58, until aortic pressure was restored to about 90% of original pressure before the test, as shown at graph point 59. Sublingual $pCO_2$ rapidly decreased from point 62, which was 300% above normal, to point 64, which was only 25% above normal.

The results in the animal model can be extrapolated to represent a human subject suffering perfusion failure, such as that associated with a gunshot wound or a severe cut from machinery or a knife. The graph 50 thus illustrates that aortic pressure rapidly decreases during blood loss, until the outflow of blood is stopped by application of pressure or other means to stop bleeding. The present invention takes advantage of these phenomena to provide methods and devices to assist a physician or other health care provider in the diagnosis and treatment of a patient having or susceptible to a condition associated with perfusion failure.

For example, although assistance from a paramedic or other person may be available shortly after the initial primary insult, it may take thirty minutes or more for the patient to reach a hospital. This lapse in time may make it difficult to accurately assess the condition of the patient and the presence and/or severity of perfusion failure. Measuring and/or monitoring sublingual $pCO_2$ according to the present invention allows the physician or other healthcare provider to readily detect the level of $pCO_2$ relative to normal, as well as the rate of change of $pCO_2$. A rapid increase in $pCO_2$ suggests that the patient has suffered a loss of blood within the last hour or so, while a high level of $pCO_2$ indicates the patient presently suffers from a low level of aortic pressure and perfusion failure. In this manner the invention can be used to assess the patient's condition, allowing for appropriate and rapid selection of an appropriate therapy.

The present invention can also be used to monitor the efficacy of reperfusion or other therapeutic regimen to treat perfusion failure in the patient. For example, if the physician, paramedic, or other emergency provider determines that a transfusion of blood or blood components is indicated, and the transfusion is successful in rapidly increasing aortic pressure (such as that illustrated in FIG. 4 from graph points 56 to 58), then this success will be reflected by a rapid drop in $pCO_2$ (as illustrated in FIG. 4 from graph points 62 to 66). It is noted that the aortic pressure increases only moderately following this rapid rise until it stabilizes; in contrast, stabilization of $pCO_2$ is slightly delayed. This delay in $pCO_2$ stabilization is likely due to a delay in the removal of $CO_2$ at the site by the increased blood flow. FIG. 4 shows that sublingual measurement of $pCO_2$ provides a good indication of the level of perfusion failure.

Figure 5:
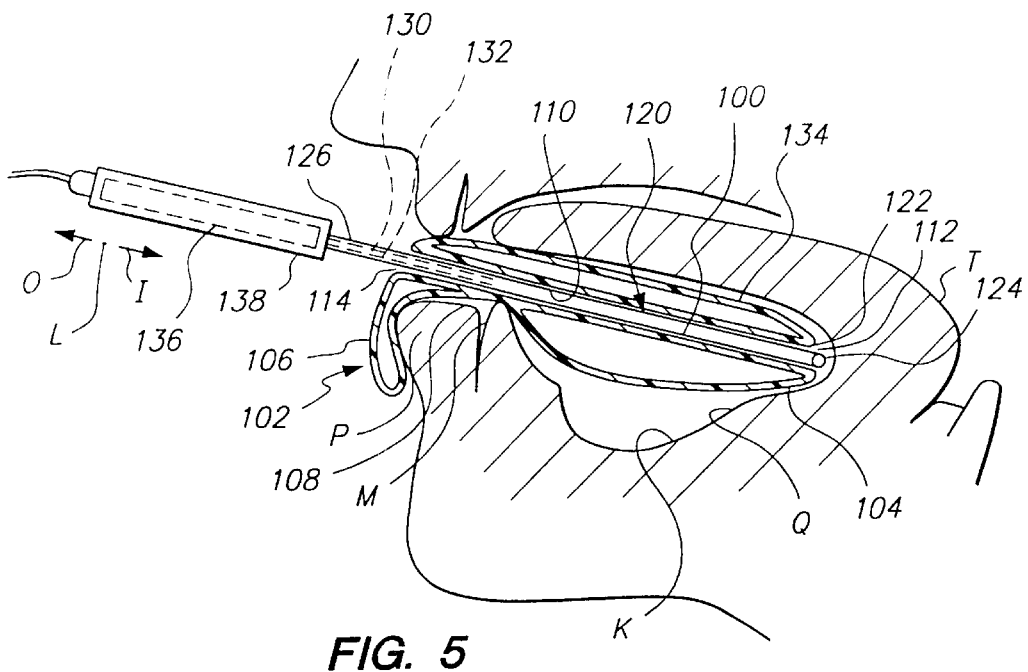
FIG. 5 is a sectional view of a sensor assembly and holder constructed in accordance with another embodiment of the invention, shown lying in a patient's mouth.

FIG. 5 shows a preferred embodiment of the device of the invention that is suitable for taking sublingual $pCO_2$ measurements. In this embodiment, sensor assembly instrument 100 is held in position by a sensor holder 102 that lies primarily in a patient's mouth. The sensor holder has a sublingual inner portion 104 that is shaped to fit under the patient's tongue T, and especially near the location where the tongue merges with the bottom or floor K of the mouth, and to lie on the bottom of the mouth. The holder has an outer portion 106 that lies outward of the inner portion and that is accessible from outside the mouth. The particular outer portion 106 lies outside the mouth and has a laterally (L) extending groove or recess 108 with groove walls that rest on the lower denture M and lower lip P of the patient.

The holder 102 forms a holder passage 110 that extends between the inner and outer portions 104, 106 of the holder. The passage has at least inner and outer ports 112, 114 and preferably extends along the entire length of the holder in the inner and outer directions I, O. The sensor assembly 100 has a frame 120 with an inner end 122 that supports a $CO_2$ sensor 124. The sensor 124 projects inwardly from the holder and substantially directly contacts the mucosal surface Q of the patient. The frame has an outer end 126 that lies outside the patient's mouth. Where required for use with the $CO_2$ sensor, a pair of electrical conductors or wires 130, 132 may extend in the frame along the length of the passage between the sensor and an electrical circuit portion 136 mounted in a handle 138, the circuit portion 136 preferably being a preamplifier but possibly being only a connector.

The holder 102 can serve at least two purposes. First the holder acts as an isolating means to isolate the mucosal surface area at and immediately around (for example, within about a centimeter or two) the measurement site (e.g., the location where the sensor touches the mucosal surface Q) from air flows in the mouth. Air flows around the sensor can sweep away some of the $CO_2$, resulting in an inaccurate reading. Furthermore, such isolation can also serve to trap moisture from the mucosal surface or from a device that adds moisture to the area where measurements are taken, thus decreasing any complications or measurement inaccuracies that may be associated with the sensor becoming too dry. To this end, the sublingual inner portion 104 of the holder preferably lies close to the walls of the mouth on opposite sides of the sensor 124, as well as above and below the sensor. The upper surface 134 of the holder is designed so the tongue T can lie on at least its inner portion, to further provide a seal and to support the tongue to avoid tiring the patient.

While the holder is an exemplary and preferred isolating means for use with the present invention, other isolating means that serve substantially the same function can be substituted or used in conjunction with the holder. For example, a sheath can surrounds the $CO_2$ sensor, where the sheath contacts the mucosal surface around the perimeter of the sensor, thereby isolating the sensor from air flow. The sensor and the sheath can be held in place by a holder similar to that described above, but with the advantage that the entire device may be of an overall smaller size (e.g., for placement in the mouth).

A second purpose of the holder is to substantially fix the position of the sensor assembly 100 and the sensor 124 so the sensor does not move during an extended period of many minutes or even hours while the $CO_2$ of the patient is being measured. A tension coil spring extending between the handle and holder, can be used to gently urge the frame 120 inwardly, where necessary. The holder 102 is preferably formed of an elastomeric material (Young's modulus of less than 50,000 psi) such as a soft rubber or soft foam, to avoid high localized pressure on the patient's mouth that could discomfort him or her.

A third, optional purpose of the holder is to prevent or slow the drying out of the $CO_2$ sensor. As observed during extended duration tests performed by applicant, $CO_2$ sensors tend to dry out. Drying out of the sensor can be associated with false readings that indicate a lower $CO_2$ level than is actually present. FIG. 17 shows $CO_2$ drift when sensors were placed in different environments during tests. Graph lines 151, 152, 153, and 154 respectively represent an environment of a 0.2% salt solution, human saliva, rat saliva, and air. The most drift was observed when the $CO_2$ sensor was used in air with substantially no isolation or added moisture.

The holder can be used to avoid drying out of the $CO_2$ sensor by isolating the sensor from air flow as discussed above. The holder can also be modified to add moisture to the area where measurements are taken. It should be noted that the $CO_2$ sensor may be used according to the present invention without a holder or humidification in the triage of a fully alert patient for a period of about one to two minutes. However, where the $CO_2$ sensor may be used in manner that renders the sensor susceptible to drying out, it is preferable to use the $CO_2$ sensor with a holder and/or to provide moisture to the site of measurement.

Figure 6:
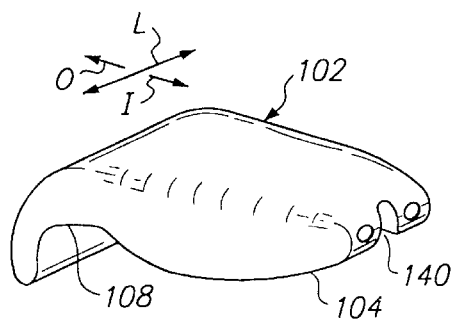
FIG. 6 is an inner isometric view of the holder of FIG. 5.
Figure 7:
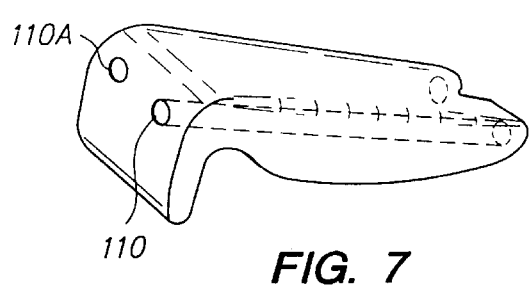
FIG. 7 is an outer isometric view of the holder of FIG. 5.

Preferably, the sensor is positioned on either side of the frenulum of the tongue. As shown in FIGS. 6 and 7, the holder 102 is thus preferably formed with a slot 140 that receives the frenulum, so the sublingual inner portion 104 can lie close to the inner end of the sublingual area and therefore closely around the $CO_2$ sensor. The particular holder shown has two passages 110, 110A that lead to areas on opposite sides of the frenulum. A thermometer can be inserted through the second passage, as the level of $CO_2$ is slightly affected by the patient's temperature. A thermometer can be incorporated in the instrument that includes the carbon dioxide sensor.

Figure 8:
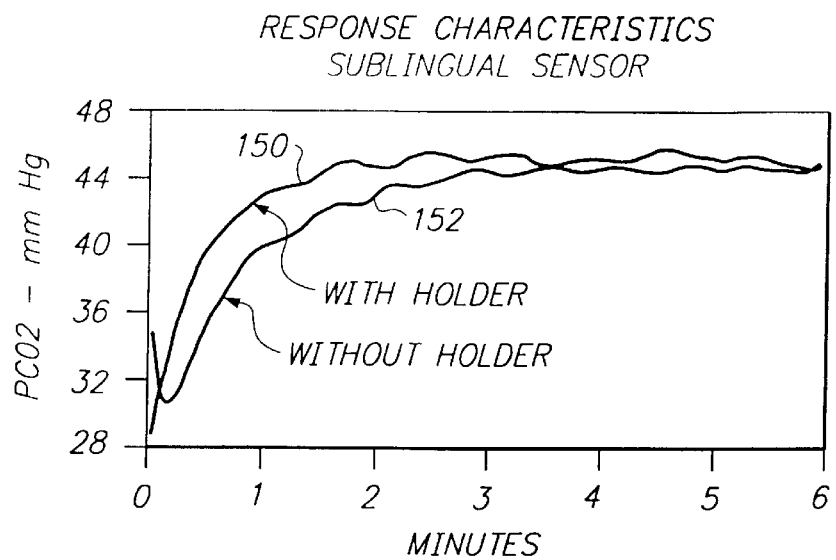
FIG. 8 is a graph that includes graph lines showing sublingual response with and without the holder of FIG. 5.

The importance of isolation of the sensor by, for example, use of the holder exemplified above, was tested in a healthy human volunteer who kept his mouth closed (around the holder and instrument) throughout the test, breathing only through his nose. The results are presented in the graph of FIG. 8, which shows $pCO_2$ (mmHg) versus time (minutes) with 150 and without 152 the holder 102. With either arrangement, it can take a few minutes for the sensed level of $CO_2$ to reach a steady state. When the holder was used, the sensed level of $CO_2$ achieved steady state after about two minutes (graph line 150). In contrast, steady state was achieved after about three minutes without the holder (graph line 152). Furthermore, the measured level of $CO_2$ was somewhat higher with the holder than without the holder. These results suggest that use of the holder resulted in a decrease in removal of $CO_2$ from the mucosal surface engaged by the sensor. Because an ill patient might not keep his mouth closed, the air flow past the sensor would be greater than in the present experiment in which the subject kept his mouth closed. In such patients, the use of the holder may prove even more important in providing sensitive, accurate, and rapid $CO_2$ measurements.

Figure 9:
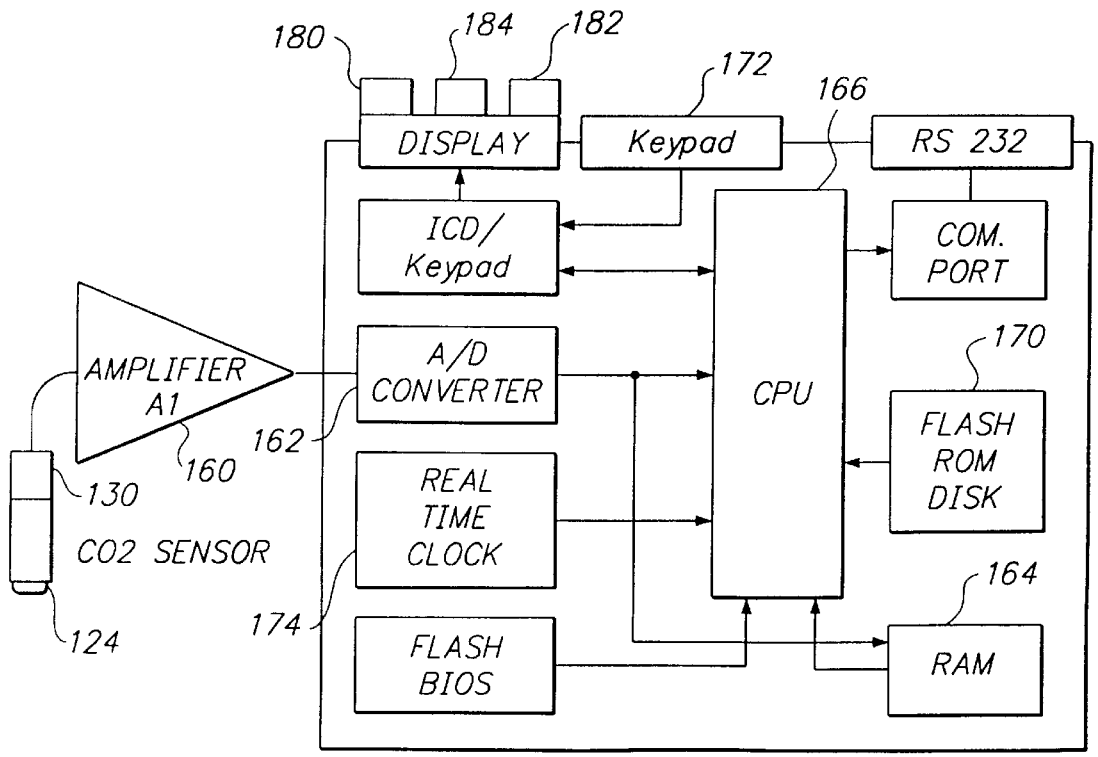
FIG. 9 is an electrical block diagram of a circuit for processing data that includes the output of the $CO_2$ sensor of FIG. 5.

The data provided by the $CO_2$ sensor may be acquired and analyzed by any appropriate means available. For example, FIG. 9 shows data acquisition circuitry that can be used to facilitate $CO_2$ data analysis. The circuit includes preamplifier 130 and amplifier 160, which deliver signals representing the $CO_2$ level to an A/D converter 162. The converter output is delivered to a memory 164 which stores the values and delivers them to a CPU, or central processing unit 166. Software for instructing the CPU to operate on the data, is contained in a memory disk 170. Pertinent information such as characteristics of the patient can be inputted through a keyboard 172. $CO_2$ levels are delivered to the CPU at a rate of five samples per second. The CPU uses this data and the elapsed time from a clock 174 to deliver signals indicating the perfusion state of the patient. If the patient's condition is poor, a red light 180 is illuminated, if the patient's condition is stable a green light 182 is illuminated, and if the patient's condition is guarded a yellow light is illuminated 184. This simplistic output is useful for moderately skilled persons such as medics in the armed forces and paramedics on ambulances. An indication of the patient's condition enables the health worker to determine whether or not the patient should be rushed to a treatment center and/or whether certain steps should be taken to enhance perfusion such as repeated depression of the chest.

The software that controls the CPU can be programmed to operate on basic principles, such as those illustrated in FIG. 10, to determine which of the three signals (red light, green light or yellow light) should be displayed. In general, a particular high level of carbon dioxide Z, as well as a low level of carbon dioxide Y are established. These high and low levels may be, for example, Z=80 mmHg and Y=50 mmHg. In addition, the CPU continually determines the rate of increase or decrease of $pCO_2$. For example, a rate of $pCO_2$ increase of more than 20 mmHg/hr. will have a very negative implication for the patient. In comparison, a rate of $pCO_2$ increase less than 20 mmHg/hr. has moderately negative or neutral implications for the patient. If the $pCO_2$ level is decreasing, or negative, this is usually positive.

As illustrated in the chart of FIG. 10, patients having a $pCO_2$ greater than Z are assigned to a first patient category 190. If the rate of change of $pCO_2$ in these first category patients is zero or positive, then the condition of the patient is assessed as being poor and the red light at 180 is energized. If the $pCO_2$ is decreasing, then the yellow light 184 is energized to indicate that the patient is in a guarded state. If the initial $pCO_2$ measurement is between the two levels Z and Y, then the patient is assigned to a second patient category 192. The condition of a second category patient is guarded, and thus the yellow light energized, unless the $pCO_2$ level is increasing at more than 20 mmHg/hr., in which case the red light is energized. For a third patient category 194, the carbon dioxide level is less than Y, and the patient is deemed to be in a stable condition. If there is a considerable change in carbon dioxide, e.g., the $CO_2$ level increases at a rate of more than 20 mmHg/hr. or decreases at a certain rate such as 10 mmHg/hr. Where the $CO_2$ level is less than Y, a considerable change in $CO_2$ level may indicate that the patient suffers from a condition associated with abnormally high blood flow.

Figure 11:
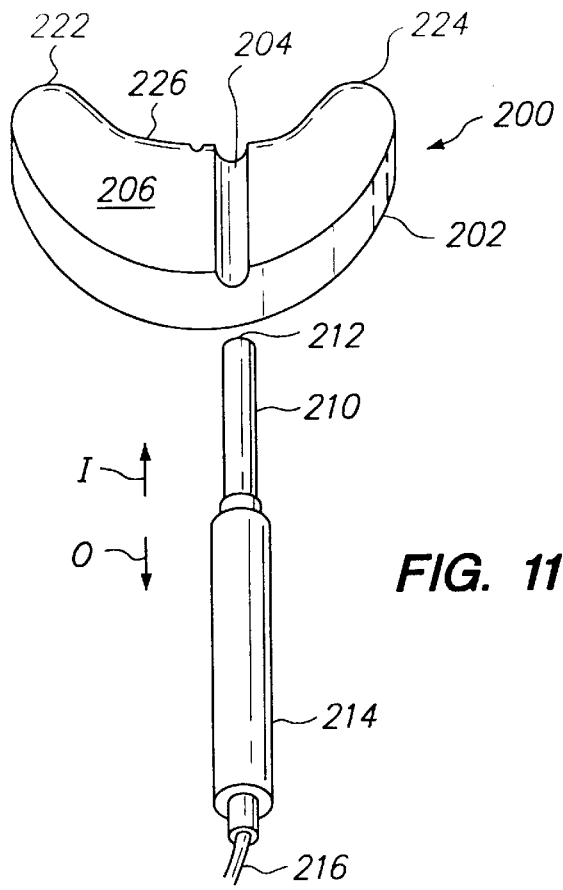
FIG. 11 is a top and outer isometric view of a holder of another embodiment of the invention.
Figure 12:
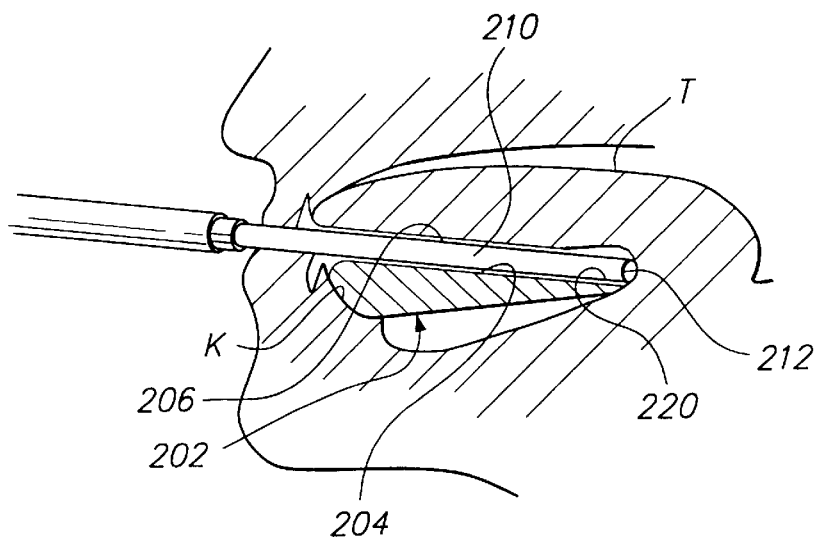
FIG. 12 is a sectional view of the holder of FIG. 11, shown lying in a patient's mouth, with a sensor assembly in place.

An additional exemplary holder useful with the present invention is illustrated in FIGS. 11 and 12. The holder 200 basically includes a body 202 of plastic and preferably of elastomeric material, with an instrument passing passage in the form of a slot 204 in its upper surface 206. A short rigid tube 210 with a carbon dioxide sensor 212 can fit in the slot. A short rigid handle 214 extends outwardly from the tube, while a flexible cable 216 extends largely outwardly from the handle. The instrument is preferably not longer than about ⅓rd meter.

FIG. 12 shows the placement of the holder body 202 lying completely within a person's mouth. The body 202 rests on the mouth floor at K with the $CO_2$ sensor 212 lying adjacent a sublingual mucosal surface area 220. The tongue T of the person lies on the body upper surface 206 and seals the area directly behind the tongue. The body has a pair of opposite sides 222, 224 (FIG. 11) that project inwardly slightly more than the middle 226 to seal the opposite sides of the sensed area 220. The rest of the body seals the region under and outward of area 220. Only the tube 210 passes between the lips. Where appropriate, the holder and sensor may be fixed together, as with wires embedded in the body.

Although applicant prefers to place the sensor in a sublingual area, the sensor can be placed within any region of the upper respiratory/digestive tract, most preferably adjacent a mucosal surface of the mouth or nose. For example, the sensor 230 can be placed at a mucosal surface W that lies between a lip X and the teeth Y of the patient (FIG. 13). The area at the rear of the upper or lower lips X, Z is a mucosal surface from which $CO_2$ is drawn by blood flow. FIGS. 13 and 14 illustrate a holder 230 suitable for use at a mucosal surface adjacent a patient's lips. In this embodiment, holder 230 is preferably of soft elastomeric material such as an elastomeric solid or a foam, or even a viscous fluid in a flexible shell. The holder isolates the mucosal surface area contacted by the sensor from air flow, thus preventing movement of the sensor and maintaining close to 100% humidity.

In another embodiment, the sensor 240 lies adjacent a mucosal surface area AA in a nares (nostril) of a patient (FIG. 15). A foam plug 242 serves as a holder that holds the sensor to position it, and that prevents air flow around the sensor. The foam plug can maintain close to 100% humidity. Only a pair of electrical wires 244 extend from the sensor through the holder. Where the $CO_2$ sensor is a fiber optical sensor, the holder can be adapted accordingly so that only the optical fiber extends from the plug.

As discussed above, it may be desirable to modify the holder or other portion of the device of the invention so as to prevent the $CO_2$ sensor from drying out. FIG. 16 shows a modified holder 260 which includes a sponge 262 containing a 0.2% salt solution (in water). Holes 264, 266 allow the weak solution to pass into the area 268 that is isolated by the holder, and where a $CO_2$ sensor 270 lies adjacent a mucosal surface. A plunger 272 can be pushed to compress the sponge and introduce the weak salt solution to the area (volume) containing the sensor to prevent dry out. Instead, a tube can be used to pass water vapor into the area 268 from a humidifier.

The $CO_2$ sensor used in the methods and devices of the invention may be any $CO_2$ sensor suitable for detection of $CO_2$ in the manner described herein. For example, the $CO_2$ sensors used in the examples herein operate by detecting a change in pH in a solution surrounding a sensor. Specifically, such sensors have a membrane that is permeable to $CO_2$, and that separates a sodium bicarbonate or carbonic acid ($HCO_3$) solution from the environment. A pH sensor in the device measures the pH of the sodium bicarbonate solution. Two exemplary $CO_2$ sensors of this type, manufactured by Microelectrode, Inc. and by Nihon Kohden (ISFET $pCO_2$ sensor), were used by applicant in the examples herein. These CO2 sensors are particularly susceptible to drying out, since solution within the sensor device can evaporate through the membrane.

Alternatively, the $CO_2$ sensor may be an optical $CO_2$ sensor. Structures, properties, functions, and operational details of fiber optic chemical sensors can be found in U.S. Pat. Nos. 4,577,109; 4,785,814; and 4,842,783, as well as in Seitz, "Chemical Sensors Based on Fiber Optics," *Anal. Chem.* 56(1):16A–34A (1984). Fiber optic sensors for monitoring $CO_2$ that may be suitable for use int he present invention include, but are not limited to, those described in U.S. Pat. Nos. 4,892,383; 4,919,891, 5,006,314; 5,098,659; 5,280,548; and 5,330,718. Other exemplary fiber optic $CO_2$ sensors are described in Peterson et al. "Fiber Optic Sensors for Biomedical Applications," *Science* 224(4645):123–127 (1984) and Vurek et al. "A Fiber Optic $pCO_2$ Sensor," *Annals Biomed. Engineer.* 11:499–510 (1983).

An especially preferred optical fiber $CO_2$ sensor is the sensor described in U.S. Pat. No. 5,714,121 ('121), which describes an optical $CO_2$ sensor and methods of manufacture of same. In general, the sensor of the '121 patent is composed of a single optical fiber having a distal tip and a proximal region for communication with a means for receiving a signal from the distal tip. Light of a predetermined wavelength is directed through the optical fiber towards the distal tip, and emitted fluorescent light returns along the fiber to be detected and converted to a $CO_2$ concentration value. A capsule, is composed of a $CO_2$-permeable silicone material, is arranged over the distal tip at a predetermined position. The capsule contains an indicator solution having a suitable pH-sensitive indicator component, generally a fluorescent dye, preferably a reference dye as well, and substantially no air. A sealing means provides a liquid-tight seal and affixes the capsule onto the distal tip. A particularly preferred system employs hydroxypyrene trisulfuric acid (HPTS) as the fluorescent dye, and a rhodamine dye as the analyte-insensitive reference dye.

Optical $CO_2$ sensors are generally used by contacting the distal end of the sensor with a mucosal surface as described herein. Light of a predetermined wavelength is directed from an external source, through the optical fiber, impinging distally on the encapsulated indicator composition. The intensity of the emitted fluorescent light returning along the fiber is directly related to the concentration of $CO_2$ in the sample, as a result of the pH-sensitive indicator material present at the fiber tip (i.e., the pH of the indicator solution is directly related to $CO_2$ concentration, as a result of carbonic acid formation). The emitted lights is carried by the optical fiber to a device where it is detected and converted electronically to a $CO_2$ concentration value. The sensor may additionally have a reference dye present in the indicator composition. The intensity of the light emitted form the reference dye may be used to compensate, via rationing, the signal obtained from the indicator.

Thus, the invention provides a method and device for assessing perfusion failure, which methods may be performed rapidly, with little equipment set up, and with minimal or substantially no invasion, and thus minimal risk of harm to the patient and an improved probability of patient compliance. The method generally involves introducing a $CO_2$ sensor into the upper digestive/respiratory tract of a patient, without passing the sensor down beyond the epiglottis where a first major intrusion would have occurred. Furthermore, the method can be performed so as to avoid even triggering the gag reflex of the patient. Measurements of $CO_2$ are taken while the sensor is held adjacent a mucosal surface in the upper digestive/respiratory tract, such as a mucosal surface of the mouth or nose, for example the area under the tongue, an area between the upper or lower lip and the teeth, or an area in the nose. A holder prevents sensor movement, while isolating the sensor area from random air flow such as inspired and expired gases which may otherwise dilute the submucosal $CO_2$, and while maintaining high humidity. The invention is useful in a variety of settings, such as in triage in emergency and disaster settings, monitoring in anesthesia, intensive care, and other acute settings in which patients may have acute perfusion failure (shock).

It is to be understood that while the invention has been described in conjunction with the preferred specific embodiments thereof, that the foregoing description as well as the examples which follow are intended to illustrate and not limit the scope of the invention. Other aspects, advantages and modifications within the scope of the invention will be apparent to those skilled in the art to which the invention pertains. All patents, patent applications, journal articles and other references mentioned herein are incorporated by reference in their entireties.

What is claimed is:

1. A device for assessing perfusion failure in a patient in a minimally invasive manner, the device comprising:

a carbon dioxide sensor means for detecting for a partial pressure of carbon dioxide (pCO2), the sensor means being adapted for lying adjacent a mucosal surface of the upper respiratory/digestive tract above the epiglottis of a patient and measuring carbon dioxide at the mucosal surface;

an isolating means for inhibiting air flow around the mucosal surface in a region surrounding the sensor means; and an indicating means operably connected to the sensor means, wherein the indicating means indicates a degree of perfusion failure of the patient associated with the detected partial pressure of carbon dioxide.

2. The device of claim 1, wherein the isolating means includes a sealing part of elastomeric material positioned to form a seal against a perimeter of the mucosal surface surrounding the sensor.

3. The device of claim 1, wherein the isolating means is a holder, the holder being designed to fit within the mouth of the patient and hold the sensor in place adjacent the mucosal surface.

4. The device of claim 3, wherein the holder is designed to contact the bottom of the tongue and the floor of the mouth of the patient, and to lie substantially against an intersection region where the bottom surface of the tongue emerges from the floor of the mouth, wherein during detecting the sensor means is positioned within the holder and adjacent a sublingual mucosal surface.

5. The device of claim 3, wherein the holder is constructed to fit between the inside of a lip and gum of the patient, wherein during detecting the sensor means is positioned within the holder and adjacent a mucosal surface isolated by the holder.

6. The device of claim 1, wherein the isolating means is a holder, the holder being designed to fit within a nares of the patient and hold the sensor in place adjacent the mucosal surface.

7. The device of claim 1, wherein the device further comprises a moisturizing means for supplying moisture to the mucosal surface adjacent the sensor.

8. The device of claim 1, wherein the sensor is a fiber optic carbon dioxide sensor.

9. The device of claim 1, wherein the indicating means comprises a circuit for generating a signal indicating a rate of change of $pCO_2$ with time.

10. A method for assessing perfusion failure of a patient, the method comprising:

placing a carbon dioxide sensor adjacent a mucosal surface of an upper digestive/respiratory tract of a patient; and measuring a partial pressure of carbon dioxide at the mucosal surface;

wherein a partial pressure of carbon dioxide at the mucosal surface of the upper digestive/respiratory tract that is substantially greater than a normal partial pressure of carbon dioxide is indicative of perfusion failure in the patient.

11. The method of claim 10, wherein the mucosal surface is within the mouth of the patient.

12. The method of claim 10, wherein the mucosal surface is within the nose of the patient.

13. The method of claim 10, wherein the partial pressure of carbon dioxide is measured using a fiber optic carbon dioxide sensor.

14. The method of claim 10, wherein said measuring step comprises:

positioning a carbon dioxide sensor means for detecting a partial pressure of carbon dioxide ($pCO_2$) adjacent the mucosal surface; and inhibiting air flow around the mucosal surface in a region surrounding the sensor means.

* * * * *